United States Patent
Wallace

(10) Patent No.: US 8,148,065 B1
(45) Date of Patent: Apr. 3, 2012

(54) LIGATION AMPLIFICATION OF NUCLEIC ACID SEQUENCES

(75) Inventor: R. Bruce Wallace, Greenbrae, CA (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 07/996,771

(22) Filed: Dec. 24, 1992

Related U.S. Application Data

(63) Continuation-in-part of application No. 07/870,221, filed on Apr. 20, 1992, now abandoned, which is a continuation of application No. 07/178,377, filed on Apr. 6, 1988, now abandoned.

(51) Int. Cl.
*C12Q 1/68* (2006.01)
(52) U.S. Cl. ....................................... 435/6.1
(58) Field of Classification Search ............. 435/6, 91, 435/91.2, 91.52; 536/23.4
See application file for complete search history.

(56) References Cited

FOREIGN PATENT DOCUMENTS

| EP | 0185494 | * | 6/1986 | ................. 435/91 |
|---|---|---|---|---|
| EP | 0200362 | * | 11/1986 | ................. 435/91 |
| EP | 0246864 | * | 11/1987 | ................. 435/91 |
| EP | 0320308 | * | 6/1989 | ................. 435/91 |
| EP | 0336731 | * | 10/1989 | ................. 435/91 |

OTHER PUBLICATIONS

Sambrook et al., Molecular, Cloning; Cold spring Harbor Press, Cold Spring Harlam NY 2nd ed (1989) p. 1.56, 1.62 & 1.70.*
Maniatis et al Molecular Cloning, Cold Spring Harlam Press, Cold Spring Harlam NY $1^{st}$ ed (1982) p. 146-47.*
Homes et al Nucleis Acid Hybridization IRL Press Wash D.C. p. 6-9.*

* cited by examiner

*Primary Examiner* — Christopher M. Babic
(74) *Attorney, Agent, or Firm* — Rothwell, Figg, Ernst & Manbeck P.C.

(57) ABSTRACT

A method is described for the identification of point mutations by a template-dependent ligation procedure. Also described is a template-dependent ligase chain reaction procedure for the amplification and detection of nucleic acid sequences.

22 Claims, 9 Drawing Sheets

```
                        ON-s2                          ON-1
                 3' TGAGGACA CCTCTTCAGACGGC 5'
                            *
(+) 5'...G CACCTGACTCCTGT GGAGAAGTCTGCCG TTACTG...3' Template
(-) 3'...C GTGGACTGAGGACA CCTCTTCAGACGG CAATGAC...5'
                            *
                 5' CACCTGACTCCTGT GGAGAAGT 3'
                        ON-s3                  ON-4

(*T-A* is the target base pair of interest)

FIGURE 2
```

LIGATION AMPLIFICATION OF NUCLEIC ACID SEQUENCES

This application is a continuation-in-part of application Ser. No. 07/870,221 filed Apr. 20, 1992 now abandoned, which is a continuation of application Ser. No. 07/178,377 filed Apr. 6, 1988 (abandoned).

Application Ser. No. 07/178,377 and application Ser. No. 07/870,221 are each incorporated herein by reference.

This invention was made with government support under Grant No. DCB-8515365 awarded by the National Science Foundation. The government has certain rights in the invention.

FIELD OF THE INVENTION

This invention relates to the identification of point mutation by a template dependent ligation procedure and to the ligase chain reaction (LAR) amplification and detection of nucleic acid sequences. The invention is described in Wu, et al. (1989(a)(b)).[1/]

[1/] See the bibliography which appears after the specification and before the claims.

BACKGROUND OF THE INVENTION

Known single nucleotide substitutions (point mutations) cause of a significant number of inherited diseases, e.g., sickle cell anemia, α- and β-thalassemia, phenylketonuria, hemophilia, $\alpha_1$-antitrypsin deficiency. Unknown point mutations may cause Huntington's chorea and cystic fibrosis (Antonarakis et al., (1985); Cooper and Schmidtke, (1986(a)(b)). No corrective measure at the molecular level is known. However, early diagnosis can often facilitate dietary and therapeutic interventions which may lead to an ameliorated clinical course of the disease. The continued development of more sensitive and precise diagnostic techniques, particularly those that enable detection of genetic diseases at the preclinical or prenatal stage, is therefore important.

Allele specific synthetic oligonucleotide (ASO) probes are widely used to detect target DNA sequences (Wallace, et al., (1979, 1981(a)(b); Conner et al., (1983)). Oligonucleotide competition techniques and stringent washing further enhance ASO probe selectivity (Nozari, et al., (1986); Wu, et al. (1989(a)).

PCR amplification and ASO hybridization have been combined to detect several DNA sequence polymorphisms, including those that cause certain genetic diseases (Saiki, R. K., et al., (1986, 1988(b); Impraim, et al., (1987); Chehab, et al., (1987); Farr, et al., (1988)).

SUMMARY OF THE INVENTION

One aspect of the invention provides a template dependent ligation method for distinguishing between single nucleotide variants of a single stranded DNA target sequence. Two oligonucleotide substrates are hybridized to the target sequence such that the 3' end of one substrate sequence is immediately adjacent the 5' end of the other. A ligase can join the juxtaposed substrates provided that the nucleotides of the junction are correctly base paired with the target strand. A single base-pair mismatch between the annealed oligonucleotides and the template suppresses or prevents ligation, thus allowing the distinction of single base-pair differences between the variant target sequences. Ligation under the mismatched condition can be further suppressed by the presence of high salt concentration, e.g., 200-500 mM NaCl or high spermidine concentration, e.g., 2-5 mM in the reaction. See Wu, et al. (1989(a)(b)), Landegren, et al. (1988) and Alves, et al. (1988).

The ligation product is increased by linear or exponential amplification using sequential rounds of template-dependent ligation. Linear amplification is accomplished by ligation of a single pair of oligonucleotides. The reaction is heated to dissociate the ligation product, and an additional round of ligation is performed. After $n$ rounds there is a $n(1+x)$ fold amplification of product, where x is efficiency of the ligation reaction. Exponential amplification utilizes two pairs of oligonucleotides, one pair complementary to the upper strand and one pair to the lower strand of a target sequence. The products of the ligation reaction serve as templates for subsequent rounds of ligation. $n$ rounds yield $(1+x)^n-1$ fold amplification of product after $n$ rounds.

DESCRIPTION OF THE FIGURES

FIG. 2 illustrates a 35 base pair template of the human sickle cell ($\beta^s$) beta globin gene in the region of the allelic base pair DNA polymorphism which is associated with sickle cell anemia and four oligodeoxyribonucleotide substrates complementary to the sickle cell allele of the gene to be used for ligation amplification.

FIG. 7A resulted from ligating $\beta^S$ substrates; FIG. 7B resulted from ligating βa substrates.

DEFINITIONS

Figure 1:
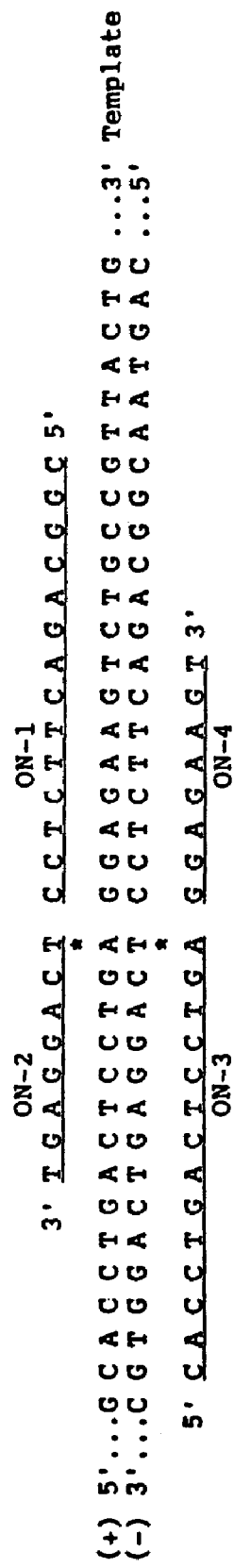
FIG. 1 illustrates a 35 base pair template of the normal human ($\beta^a$) beta globin gene in the region of the allelic base pair DNA polymorphism associated with sickle cell anemia and four oligodeoxyribonucleotide substrates complementary to the normal beta globin allele of the gene to be used for ligation amplification.

Point mutation--a single nucleotide substitution in the sequence of a gene.

Target sequence--a DNA sequence that may or may not include a point mutation.

Template--a single stranded DNA sequence that includes a target sequence.

Substrate--an oligonucleotide sequence complementary to a region of a template which, when annealed to said template, can be ligated to an adjacently annealed second substrate.

Template dependent ligation--ligation of substrates annealed to a complementary template.

Template independent ligation--any ligation of oligonucleotides which is not a function of the degree of substrate-template complementarity, e.g., blunt end ligation of DNA sequences resulting from the substrate hybridization.

DETAILED DESCRIPTION OF THE INVENTION

1. Template Target Sequences

Templates useful in the invention may be obtained from various sources, e.g., any natural or synthetic DNA or RNA. The invention has particular applicability to templates derived from cloned DNA and genomic DNA or RNA derived from human blood or tissue. Such templates may include one or a plurality of the same or different sequences which may be amplified simultaneously. Single stranded templates are obtained from double stranded DNA by known denaturing techniques, for example, by heating at temperatures from about 80° to 105° C. for about 1 to 10 minutes or by enzymes. See, e.g., Wallace, et al. (1980).

Target sequences include, for example, the causative point mutations for genetic diseases such as sickle cell anemia, β and β-thalassemia, phenylketonuria, hemophilia, or $β_1$-antitrypsin deficiency.

2. Substrates

Substrates useful in the invention are oligonucleotide sequences complementary to sequences which immediately flank each side of a variant nucleotide in a target sequence. Substrates may be synthesized by known methods using commercially available synthesizers such as Applied Biosystems 380B automated DNA synthesizers. See Wu, et al. (1989). Substrate length depends on various factors including the temperature of the reaction, pH, and complexity of the target sequence. Substrate sequences of from about 4 to about 100 nucleotides are generally useful particularly at higher reaction temperatures. In the preferred practice of the invention, the substrates are sequences of from about 8 to about 25 nucleotides.

Typical substrate pairs useful for the template-dependent ligation by T4DNA ligase are set forth in Table 1.

TABLE 1

| DNA Sequence of Synthetic Oligonucleotide Substrates | | | | |
|---|---|---|---|---|
| Oligonucleotide[a] | | Role[b] | Gene | Sequence (5'-> 3') |
| (SEQ ID 1) | ON1 | S | $β^A$ and $β^S$ | CGGCAGACTTCTCC |
| (SEQ ID 2) | ONA2 | S | $β^A$ | TCAGGAGT |
| (SEQ ID 3) | ONA2$^a$ | S | $β^A$ | TCAGGA |
| (SEQ ID 4) | ONS2 | S | $β^S$ | ACAGGAGT |
| (SEQ ID 5) | ONS2$^a$ | S | $β^S$ | ACAGGA |
| (SEQ ID 6) | ONA3 | S | $β^A$ | CACCTGACTCCTGA |
| (SEQ ID 7) | ONS3 | S | $β^S$ | CACCTGACTCCTGT |
| (SEQ ID 8) | ON4 | S | $β^A$ and $β^S$ | GGAGAAGT |
| (SEQ ID 9) | ON4$^a$ | S | $β^A$ and $β^S$ | GGAGAA |
| (SEQ ID 10) | Hβ19A | T | $β^A$ | CTCCTGAGGAGAAGTCTGC |
| (SEQ ID 11) | Hβ19S | T | $β^S$ | CTCCTGTGGAGAAGTCTGC |
| (SEQ ID 12) | Hβ23A' | T | $β^A$ | CGGCAGACTTCTCCTCAGGAGTC |
| (SEQ ID 13) | Hβ23S' | T | $β^S$ | CGGCAGACTTCTCCACAGGAGTC |

[a]Oligonucleotides are used as pairs for the specific detection of template target sequences (FIG. 1). ON1/ONA2 and ONA3/ON4 are substrate airs for the normal β-globin gene. ON1/ONS2 and ONS3/ON4 are substrate pairs for the sickle cell globin gene.
[b]Role of the oligonucleotide is either as ligation substrate (S) or template (T).

Ligases

Table 1 substrates are complementary to the human β-globin gene in the region encompassing the sickle cell mutation (Wu (1989(a)). The two oligonucleotides in each pair anneal to the β-globin template at adjacent positions such that the 3' end of one oligonucleotide (ONA1, ONA3, or ONS3) and the 5' end of the other (ONA2, ONS2, or ON4) form a ligatable junction (FIG. 1).

In this design, the site of the DNA sequence variation in the template base-pairs with either the 3' end nucleotide or the 5' end nucleotide of the substrate oligonucleotide, depending on which strand, (+) or (−), serves as the template for ligation. The ON1/ONS2 and ON1/ONA2 pairs both hybridize to the coding strand. ONS2 and ONA2 differ from each other by a single nucleotide at the 5' end, ONS2 being complementary to the sickle cell allele and ONA2 to the normal allele. Similarly, ONS3/ON4 and ONA3/ON4 pairs hybridize to the noncoding strand, with ONS3 and ONA3 differing by a single nucleotide at their 3' ends.

When a double-stranded nucleic acid template is used, symmetry requires that ON2 be complementary to ON3, except for differences in length. Likewise ON1 is complementary to ON4, except for differences in length. As seen in FIG. 1, ON1 is complementary to ON4. Therefore in cases where double-stranded nucleic acid template is to be used, the flanking oligonucleotides can be double-stranded, for example:

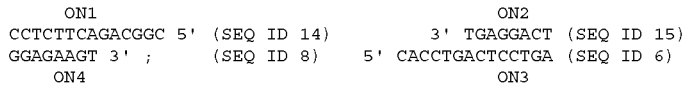

```
     ON1                            ON2
CCTCTTCAGACGGC 5'  (SEQ ID 14)       3' TGAGGACT (SEQ ID 15)
GGAGAAGT 3' ;      (SEQ ID 8)    5' CACCTGACTCCTGA (SEQ ID 6)
     ON4                            ON3
```

Under appropriate conditions, a single base-pair mismatch between the substrate and the template at the substrate pair junction prevents ligation. See Wu, et al. (1989(a)). ON1/ONA2 and ONA3/ON4 constitute the substrate pairs for detection of the normal β-globin sequence. ON1/ONS2 and ONS3/ON4 are the substrate pairs for detection of the sickle cell sequence. The specificity of the ligation reaction depends on the specificity of the T4 DNA ligase.

It has been found that inclusion of at least 200 mM NaCl in amplification reaction mixtures almost completely suppresses mismatch ligation. Therefore, with reference to FIG. 1, if the target site of the template DNA contains a nucleotide which is not complementary to 5' end of ON2 or the 3' end of ON3, the mismatch of nucleotides prevents any significant ligation which would have caused formation of a 22 base long product (22-mer). The absence of such ligation product thereby indicates that the target bases of interest are not present on the particular template. For example, if the template in FIG. 1 were the sickle cell (BS) gene in which bases A and T are interchanged at the target base site, there would be no ligation of either ON2/ON1 or ON3/ON4 as depicted in FIG. 1. No 22 nucleotide amplification ligation product would be formed.

For linear amplification either of the two substrate pairs may be used. In the exponential amplification scheme, template-dependent ligation of either ON1/ON2 or ON3/ON4 pairs forms a 22-mer whose sequence is complementary to the ligation product, of the other substrate pair. For example, an ON1-ONA2 ligation product would be complementary to ONA3/ON4 substrate pairs, and ONS3-0N4 ligation product would be complementary to ON1/ONS2 substrate pairs. The ligation pair products then serve as template for the ligation of the complementary substrate pair, producing additional templates for further ligation (FIG. 2). The 22-mer as formed is hybridized to its template. If a thermophilic ligase is used, denaturing may be accomplished by heat. Otherwise, addition of fresh non-thermophilic enzyme is necessary to initiate the next round of amplification.

In n rounds, the amount of 22-mer would increase at an exponential rate according to the equation, $(1+x)^{(n-1)}$, where x is the ligation efficiency.

A template dependent ligase is required for the practice of the invention. Appropriate ligases include T4-DNA ligase, *E. coli* DNA ligase and *T. thermophilus* DNA ligase. With regard to ligation, any ligase capable of joining substrates in a template ligation reaction may be used. Such ligases include those derived from thermophilic ligations permitting ligation at high temperatures. See generally Zimmerman (1983), Takahashi, et al. (1986) and Ferreti, et al. (1981).

Ligation Amplification Systems

In the exemplified embodiments of the invention, ligation reactions were carried out in 50 mM Tris HCl (pH 7.6), 10 mM $MgCl_2$, 1 mM ATP, 1 mM DTT, 200 mM NaCl and 5% polyethylene glycol (PEG) with 5-10 μM of each substrate oligonucleotides mixed with a small amount of radioactively labeled 3' oligonucleotide substrate (100,000-300,000 cpm) and the indicated amount of template. Plasmid and genomic DNA template reactions were heated to 100° C. for 5-10 minutes, followed by the addition of T4 DNA ligase (1 unit; BRL). All ligation reactions were carried out at 30° C. for a specified incubation time and terminated by heating to 100° C. for 5 minutes.

Any person skilled in the art will know and be competent to practically utilize reaction conditions effective to achieve the ligation steps of this invention.

In general, ligation reactions pursuant to this invention are carried out at a temperature of 15° C. to 75° C. for about 1 to 300 minutes. A template concentration of 0.02 mM to 1 mM is preferred. The template-substrate hybridizations are stoichiometric. A stoichiometric substrate excess greater than the fold of at least $10^6$ with regard to template concentration is preferred to achieve amplification. A ligase concentration of about 0.1 units/μl to about 1,000 units/μl is appropriate.

Suppression of Blunt End Ligation

In solution and if allowed to anneal, a mixture of ON1, ON2, ON3, and ON4 or similar substrates form two partial duplexes, ON1 annealing to ON4 and ON2 annealing to ON3 (FIG. 1). These duplexes possess a phosphorylated blunt end that could be ligated to form template-independent ligation products (Zimmerman, et al. (1983); Phiffer, et al. (1983)). Of the four possible blunt end ligation products, two are indistinguishable from the template-dependent products and thus are a potential problem if not suppressed. The initial rounds are important, because even a small amount of template-independent ligation product would be amplified to become a significant component of the final signal. Blunt end ligation is inhibited by NaCl or Pi at concentrations above about 200 mM. In the preferred practice of this invention, 200 mM NaCl is included in the amplification reactions. See Hayashi, et al. (1986).

EXAMPLE I

All oligodeoxyribonucleotide ligation reactions on oligonucleotide templates were carried out, unless otherwise indicated, in 50 mM Tris HCl (pH 7.6), 10 mM $MgCl_2$, 1 mM DTT (dithiothreitol), 1 mM ATP, 200 mM NaCl and 5% PEG (polyethyleneglycol) with 5-10 μm of each substrate oligonucleotide mixed with a small amount of radioactively labeled 3' oligonucleotide substrate (100,000-300,000 cpm) and the indicated amount of template.

Plasmid and genomic DNA template reactions are initiated following 5-10 minutes of boiling, cooling on ice and the addition of ligase (1 U; BRL). Unless otherwise indicated, all ligation reactions are withdrawn for electrophoresis and optionally treated with calf intestinal alkaline phosphatase (1-5 U) for 1-2 hours.

Linear amplification ligation of nucleic acid sequences is carried out by repeatedly using the original nucleic acid template (oligo, plasmid or genomic DNA) in each round of amplification. Only one flanking oligonucleotide set complementary to the appropriate oligonucleotide template to one strand of duplex plasmid or genomic DNA template is used. For example, either the ON1 and ON2, or ON3 and ON4 set is used in the amplification rounds but not both.

To linearly amplify a sequence of the 5' strand of the human sickle cell ($β^S$) β-globin gene as shown in FIG. 2, the above reaction mixture further containing 1 mM ON1, 1 mM 5' phosphorylated ONA2 (SEQ ID 2), and 0.1 pmoles of $β^S$ (Hβ19S) template was prepared. If double-stranded template is used, it must be denatured by boiling the reaction mixture at about 90-100° C., for 10 minutes.

Each round of ligation is initiated by adding 1 unit of ligase to the reaction mixture on ice. The mixture is incubated for about 30 minutes at 30° C., or for a longer time if template concentration is low.

The first round, and all subsequent rounds, is terminated by quickly heating the reaction mixture to 100° C. for 5 minutes to inactivate the ligase and dissociate the ligated product strand (ON1/ON2) from the template. This frees the template for subsequent amplification rounds. Before the next round, the reaction mixture is centrifuged for 10 seconds and immediately cooled to about 0° C. At this point, there is approximately one ON1/ON2 ligation product present for each copy of the template.

Another unit of enzyme is added to the reaction mixture to initiate a second round of ligation. Because a molar excess of flanking oligonucleotides ON1 and ON2 are added to the initial reaction mixture, more flanking oligonucleotide substrates are not added. The reaction mixture is then incubated as in the first round, boiled to dissociate template from the ligation product, and cooled. At this point, there are approximately 2 copies of ON1/ON2 ligation product present for each copy of template.

Fresh enzyme is added to initiate another round. The steps of incubating, boiling to dissociate template from product, cooling, and adding fresh enzyme are repeated for as many rounds as necessary to produce a detectable signal.

Detection of the ON1/ON2 ligation product can be accomplished in several ways. ON1 and/or ON2 can be labeled with radioactive or nonradioactive labels and separated from the reactants by gel electrophoresis, such that ligation product is determined by detecting the presence of label in a position in the gel corresponding to the expected product size.

ONA2, ONS2, and ON4 are phosphorylated at their 5' ends with either radioactive (γ [$^{32}P$] ATP 6000 Ci/mmol; New England Nuclear) or nonradioactive ATP via a kinase reaction. The unlabeled 5' phosphorylated substrates are used following incubation in a boiling water bath for 20 minutes to inactive kinase. Internal radioactively phosphorylated oligonucleotide products are separated from unreacted ATP and other reaction products with an ion exchange chromatography (DE-52 cellulose-Whatman). The radioactive phosphorylation reaction yields products with approximately $10^8$-$10^9$ cpm/pmol specific activity.

Detection and quantitation of ligation product by polyacrylamide gel electrophoresis is carried out by mixing samples from ligation reactions with Ficoll loading buffer and subjecting the mixture to electrophoresis in TBE (89 mM Tris, 89 mM Borate, 2 mM EDTA) in 20% polyacrylamide (Bio-Rad) urea (7M) gel at 600 V. for 1.5 hours. The gel is then wrapped in Saran Wrap and autoradiographed between two Lightning Plus intensifier screens (DuPont) overnight. Quantitation of ligation product is obtained either from densitometric measurements of the autoradiograph or directly from the gel via an AMBIS Radioisotope Scanning System II (Automated Microbiology System, Inc.). In the latter instance the polyacrylamide gel is first fixed in a 5% acetic acid solution for 10 minutes.

The ON1/ON2 ligation product can also be detected by hybridizing the product containing solution to a substrate containing an immobilized complementary DNA or RNA sequence under conditions whereby the ON1/ON2 ligation product will hybridize to the complementary sequence, but neither ON1 nor ON2 will. Bound label indicates presence of ligation product. The ligated product can also be detected in a subsequent round of ligation employing a radiolabeled counterpart substrate set (ON3/ON4). In the case where ligated ON3/ON4 is to be detected, labeled ON1/ON2 would be used.

The product level after n-number of rounds of linear amplification-ligation is equal to $\bar{1}$(n)(1+x) where x is the efficiency of the ligation. x ranges from 0 to 1, where $\bar{1}$ is equivalent to 100% ligation.

EXAMPLE II

Figure 4:
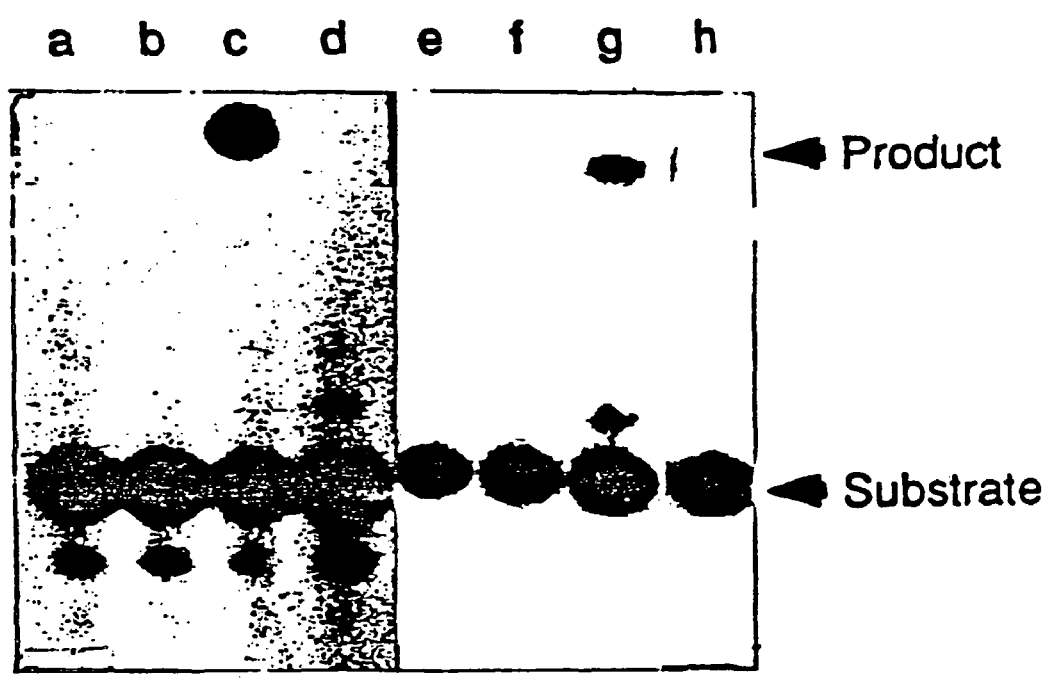
FIG. 4 is a photograph of an autoradiogram of product of linear ligation amplification of $\beta^S$ substrates on sickle cell (lanes c and g) and normal beta globin (lanes d and h) oligonucleotide templates.

ON1/ONS2* and ONS3/ON4* were ligated linearly on oligonucleotide templates using the above methodology. ONS2* and ONS4* are the same as ONS2 and ON4 except that they are only 6 nucleotides long. 10 pmoles of $^{32}P$-5' phosphorylated ONS2* and unlabeled 5' OH—ON1 (lanes a-d) or $^{32}P$-5' phosphorylated ON4* and unlabeled 5' OH—ONS3 (lanes e-h) were ligated on 19 base long or 23 base long oligonucleotide template respectively at 30° C. for 30 minutes with 1 U. of T4 DNA ligase in 10 μl reaction volume. FIG. 4 shows the results of the ligation amplification reactions described below. Samples in lanes a and e not treated with enzyme and samples in lanes b and f, without template, serve as negative controls. 1 pmole of the following oligonucleotide template was used: Hβ19S (c); Hβ19A (d); Hβ23S' (g); and Hβ23A' (h).

As seen in FIG. 4, the expected ligation involving sickle cell template and sickle cell substrates occurred (lanes c and g); ligation of normal (A) beta globin substrates did not occur on the sickle cell template (lanes d and h).

EXAMPLE III

Figure 3:
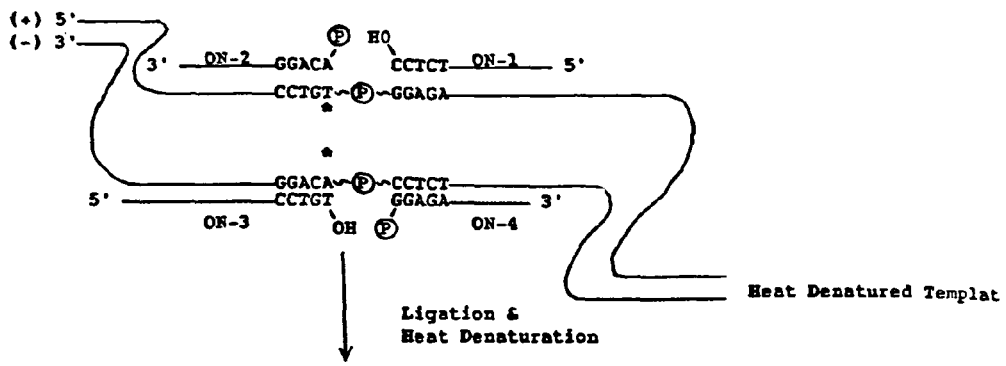
FIG. 3 is a schematic diagram of template dependent exponential ligation amplification.
Figure 3:
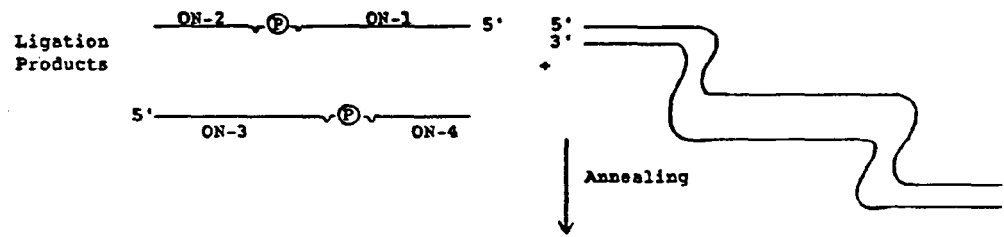
Figure 3:
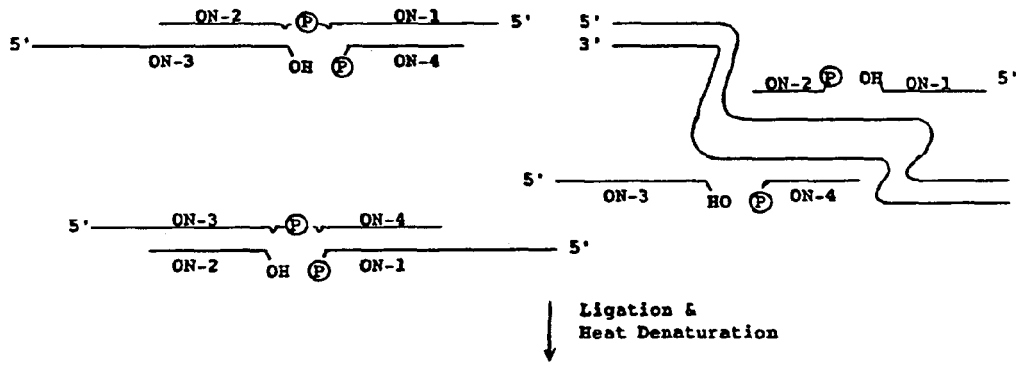
Figure 3:
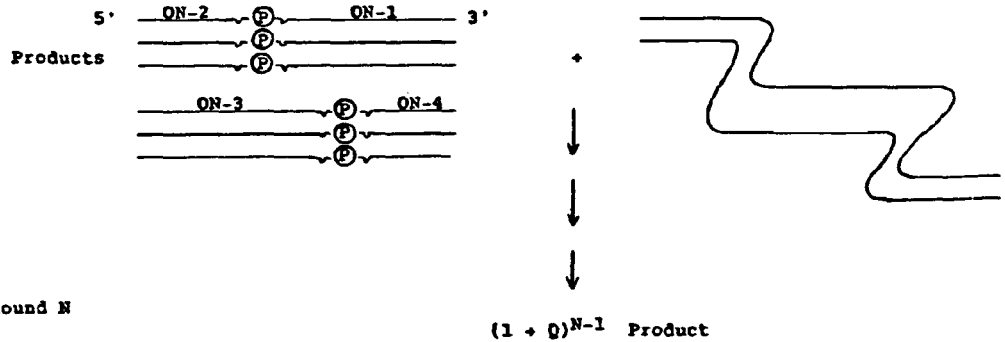

The method of the present invention can also be used to exponentially amplify nucleic acid sequences. The major difference between exponential amplification ligation and the above-described linear amplification ligation is that all four flanking oligonucleotides (ON1/ON2, and ON3/ON4) are present as substrates during each reaction round. The ligation product of either flanking oligonucleotide set serves as the template for the other flanking oligonucleotide set in subsequent amplification rounds as shown in FIG. 3.

Radioactively labeled substrate for detection can be included in the starting materials or can be added in the last round.

As is also the case for linear amplification, an estimation of the number of amplification rounds needed to produce a detectable signal is preferably made before carrying out the exponential amplification. After n rounds, the product formation equals $(1+x)^n-1$ where x is ligation efficiency. The following table indicates the relative amounts of ligation products present after N cycles, assuming 100% efficiency at each cycle.

| Round | Fold Amplification $(2)^n-1$ |
|---|---|
| 0 | 0 |
| 1 | 1 |
| 2 | 3 |
| 3 | 7 |
| 4 | 15 |
| 5 | 31 |
| 6 | 63 |
| 7 | 127 |
| 8 | 255 |
| 9 | 511 |
| 10 | 1023 |
| . | . |
| . | . |
| . | . |
| 15 | 32,767 |
| . | . |
| . | . |
| . | . |
| 20 | 1,048,575 |
| 21 | 2,097,141 |
| . | . |
| . | . |
| 25 | 33,554,431 |

For example, if $10^6$-fold of product amplification is required at a certain specific radioactivity, approximately 20 rounds of amplification are needed ($2^{20}$-$10^6$), assuming 100% ligation efficiency.

Near perfect ligation efficiency is present at later rounds where the primary template source is ligated flanking oligonucleotide products. During early rounds, ligation efficiency may be lower depending upon reaction conditions, types of ligase used, and source of template.

Each round of exponential ligation is started by adding one unit of enzyme to the reaction mixture on ice. In the first and each subsequent round of amplification, the reaction mixture with the added enzyme is incubated for about 30 minutes at 30° C. or for a longer period of time if template concentration is low. At the end of each round, the reaction mixture is quickly brought to boiling temperature for 5 minutes to inactivate the enzyme and dissociate the product strands from the template strands. Then the reaction mixture is centrifuged for 10 seconds and immediately cooled to about 0° C.

Another unit of T4 ligase is then added to initiate the second round of amplification. The mixture is then incubated, boiled, and cooled as above. At this point there are 3 copies of template present for each copy present at the beginning of the reaction. All subsequent rounds of amplification are carried out by the same sequence of steps for as many times needed in order to produce a detectable signal.

The progress of the amplification may be monitored by withdrawing from the reaction mixture an approximately 10 µl aliquot of reaction mixture during predetermined rounds. The withdrawn material is heat inactivated and is then combined with 2 to 3 µl of loading buffer. 2 µl of this buffered mixture is then loaded onto a 20% polyacrylamide gel and the gel is electrophoresed for one hour at 600V and then autoradiographed overnight with two DuPont Lightening-Plus intensifier screens.

Using these methods and the reaction mixture described in Example 1, 6.67 nM of oligonucleotide template, Hβ23S' and Hβ23A', was amplified with T4 DNA ligase and 1.33 mM of each flanking oligonucleotide substrate: $^{32}$P-5' labeled ONS2 ($10^6$ cpm); $^{32}$P-5' labeled ON4 ($10^6$ cpm); 5' OH—ON1; and 5' OH—ONS3. 1 U of T4 DNA ligase was used to initiate each round. Six rounds of ligation amplification were carried out.

Figure 5:
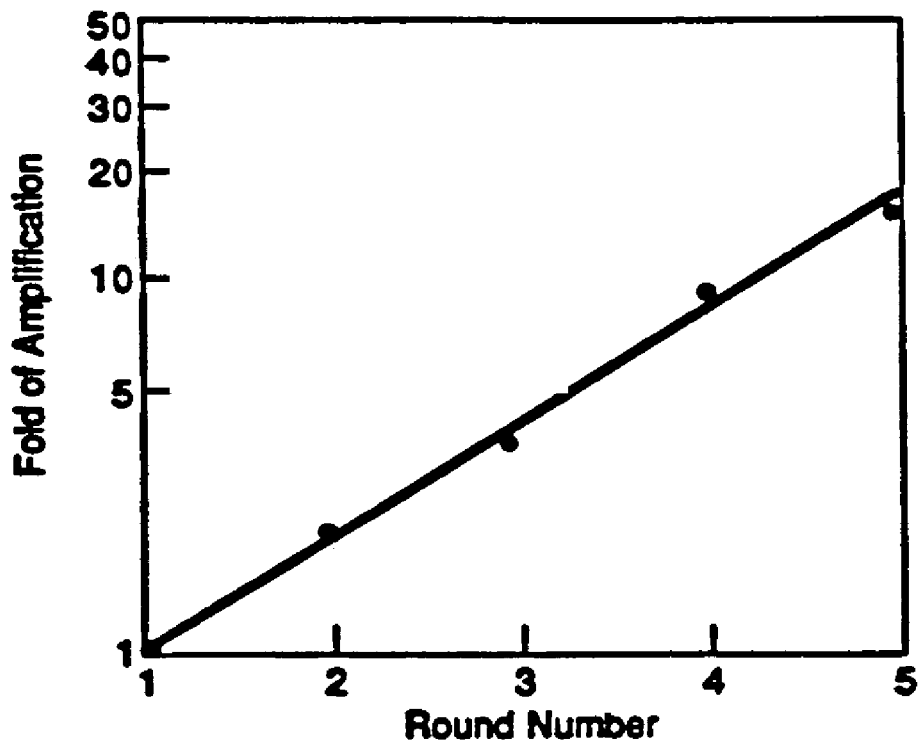
FIG. 5A is a photograph of autoradiograms of reaction products from six rounds of exponential ligation amplification of substrates designed to be complementary to the sickle cell gene sequence using sickle cell (Hβ23S') and normal (Hβ23A') oligonucleotide template.
FIG. 5B is a logarthmic plot of fold of amplification versus number of exponential ligation amplification rounds performed.
Figure 5:
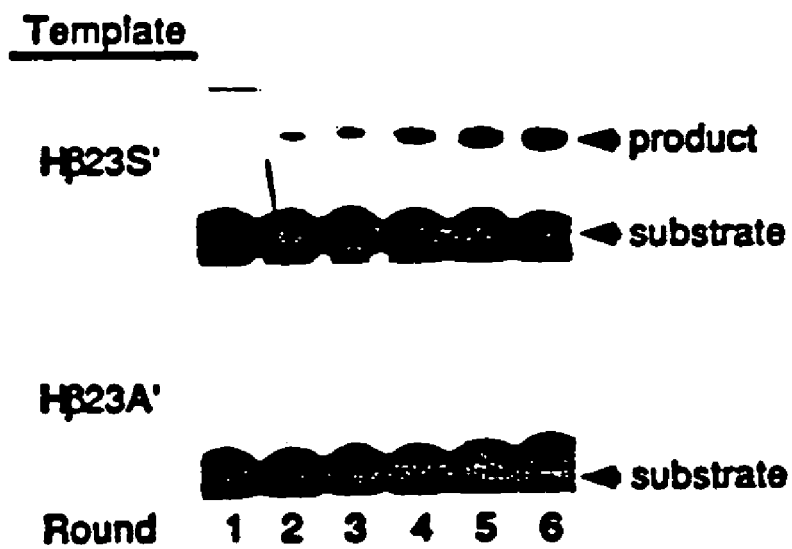

FIG. 5A is an autoradiogram showing the results of monitoring each round of reaction for each template. In rounds 2-6, the ligation reaction was specific for the Hβ23S' template containing the sickle cell sequence. The flanking oligonucleotide substrates were not able to ligate in the presence of the Hβ23A' template.

Products of the exponential ligation method approximately double with each round. FIG. 5B shows a logarithmic plot of amplification folds as a function of the number of rounds of ligation amplification performed. A straight line was obtained with a calculated efficiency of 0.98. Thus, in each round, the ligation product of the preceding round serves effectively as the template for further oligonucleotide ligation.

The methods of the present invention can also be used to detect plasmid and genomic DNA sequences as illustrated in the following example.

EXAMPLE IV

Templates for amplification ligation were derived from plasmids pHβ$^a$ and pHβ$^s$ which contain respectively an approximately 4.4 kbp normal (β$^a$) and sickle cell (β$^s$) beta globin gene insert. All DNA preparations were performed according to a modified Triton X-100 procedure followed by Proteinase K and RNase treatment.

The plasmid DNA was treated with restriction enzyme (Bam H1 and/or Taq 1) and Exonuclease III (Exo III) prior to serving as template in ligation reactions as follows: pHβ$^a$ and pHβ$^s$ were separately digested with Bam H1 (5 U/pmol) for 2 hours at 37° C. and terminated in a boiling water bath for 5 minutes. Exo III (100 U/pmol) was then added to the reaction mixture with DTT to make a final concentration of 1 mM. The mixture was incubated 4 hours at 37° C. Phenol-chloroform extraction was performed for final purification.

1 nm of each of the two resulting templates (pHβ$^s$ and pHβ$^a$) was then amplified exponentially using T4 DNA ligase and the reaction mixtures and methods described in Examples 1 and 3 except that the total volume of each reaction was 100 µl. 500 nM of each of the following flanking oligonucleotide substrates was used: $^{32}$P-5' labeled ONS2 ($10^6$ cpm), $^{32}$P-5' labeled ON4 ($10^6$ cpm), 5' OH—ON1, and 5' OH—ONS3. After the 10th, 12th, and 14th amplification rounds, a 4 µl aliquot was withdrawn from the reaction mixture and analyzed by electrophoresis and autoradiography.

Figure 6:
FIG. 6 is a photograph of an autoradiogram of the product of from 10-14 rounds of exponential ligation amplification using templates from plasmids containing normal (lanes g-i) and sickle cell (lanes d-f) beta globin gene using substrates complementary to the sickle cell beta globin gene sequence (FIG. 2) and normal beta globin gene sequence (FIG. 1).

FIG. 6 shows the results of the ligation amplification. Product in lanes a-c resulted from reactions not including template; product in lanes d-f resulted from reactions containing pHβ$^s$ template; and product in lanes g-i resulted from reactions containing pHβ$^a$ template. Reaction products in lanes a, d, and g were withdrawn and analyzed after 10 rounds; products in lanes b, e, and h were analyzed after 12 rounds; and products in lanes c, f, and i were analyzed after 14 rounds.

No detectable ligation product is seen from the reactions involving pHβ$^a$ which contained the normal beta globin sequence (g-i) or in lanes without any template (a-c). The pHβ$^s$ sickle cell template was significantly amplified, with the detectable signal noticeably increasing between 10 (lane d), 12 (lane e), and 14 (lane f) amplification rounds.

For the 1 nM plasmid template used in the reactions, approximately 10 rounds of ligation amplification were necessary to generate a detectable signal corresponding to approximately a 50-fold amplification. In contrast, only about 3-6 rounds of amplification are needed to amplify oligonucleotide template of the same concentration to obtain the same fold amplification.

EXAMPLE V

Normal (β$^a$/β$^a$) sickle cell disease (β$^s$/β$^s$), and sickle cell trait (β$^a$/β$^s$) genomic DNA samples were isolated from blood specimens of appropriate donors. Beta thalassemia major DNA was prepared from EBV transformed lymphocytes in culture (GM 2267 cells from NIGMS Human Genetic Mutant Cell Repository, Camden, N.J.). Thalassemia DNA was subsequently isolated from cultured cells. All DNA preparations were performed according to a modified Triton X-100 procedure followed by Proteinase K and RNAse treatment.

Genomic DNA (5 μg) was digested with Taq 1 restriction enzyme (10 U/μg) (Boehringer Mannheim) overnight at 65° C. and followed by Bam H1 digestion (10 U./μg) (Bethesda Research Laboratory) for 8 hours at 37° C. Subsequently Exo III nuclease (100 U./pmol) was added to the reaction mixture along with DTT to make 1 mM final concentration and the reaction was incubated for 5 hours at 37° C. Phenol-chloroform extraction was carried out for final purification.

Ligation conditions for genomic DNA and for plasmid DNA are identical except that the total volume of the reaction for the genomic DNA sample is 200 μl.

Genomic DNA from β thalassemia, sickle cell, and normal DNA were amplified using 200 nM of the following sets of flanking oligonucleotides: $^{32}$P-5' labeled ONS2 (10$^6$ cpm)/$^{32}$P-5' labeled ON4 (10$^6$ cpm)/5' OH—ON-1/5' OH—ONS3; and $^{32}$P-5' labeled ON2 (106 cpm)/$^{32}$P-5, labeled ON4 (10$^6$ cpm)/5' OH—ON-1/5' OH—ON3.

5 μg of genomic DNA contains approximately 500,000 molecules of homozygous single copy gene. When used as a template in a 200 μl reaction mixture, 5 ug of DNA is equivalent to 2.5×10$^{-14}$M with respect to template. This concentration is well below the apparent K$_m$ of T4 DNA ligase for ligation template. The enzyme activity is therefore expected to be slowed considerably. To overcome this kinetic constraint, early rounds of the ligation were incubated for a longer time period. The ligation time for initial rounds was 5 hours. With subsequent rounds, the incubation time was gradually reduced to 30 minutes. (Rounds 1-5=5 hours; round 6-10=4 hours; rounds 11-15=3 hours; rounds 16-20=2 hours; round 20-30=1 hour; and rounds 30+=30 minutes.) Each round however was not allowed to exceed 5 hours in order to avoid accumulation of blunt end products.

Figure 7:
FIGS. 7A and 7B are photographs of autoradiograms resulting from amplification of human genomic DNA using B thalassemia (lanes a, b), sickle cell (lanes c, d), and normal β globin (lanes e, f) DNA template.
Figure 7:
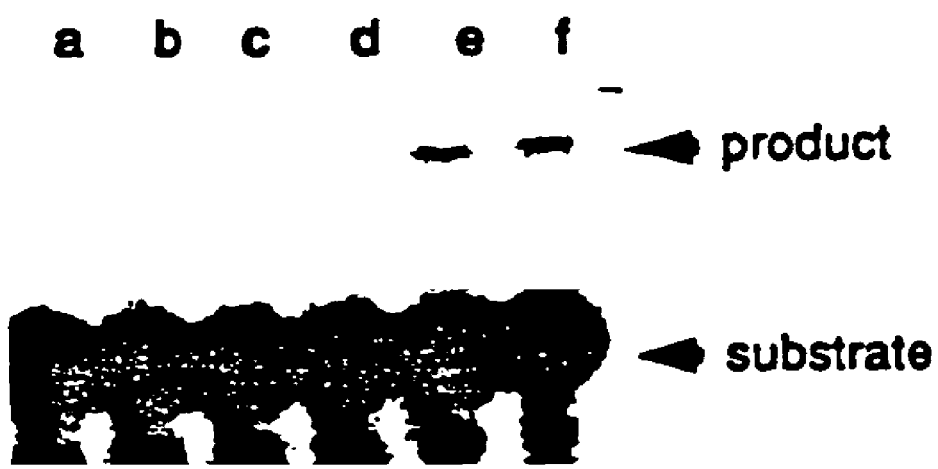

FIGS. 7A and 7B show the results of 70-75 rounds of exponential amplification using these templates and flanking substrates. FIG. 7A contains amplification product resulting from the β$^s$ flanking oligonucleotide set; FIG. 7B contains amplification product resulting from the β$^a$ flanking oligonucleotide set. Lanes a and b of each autoradiogram contain reaction product using β thalassemia genomic DNA template; lanes c and d contain product from sickle cell genomic DNA template, and lanes e and f contain product using normal beta globin genomic DNA template. Template in lanes a, c, and e was amplified 70 rounds; template in lanes b, d, and f was amplified 75 rounds. The expected product bands appear in lanes c and d of FIG. 7A (sickle cell template and flanking oligonucleotides) and in lanes e and f of FIG. 7B (normal beta globin template and flanking oligonucleotides). β-thalassemia DNA (lanes a and b) and mismatched genomic DNA and substrates both showed absence of signal.

This example thus demonstrates that the ligation amplification methods of the present invention can be used as a diagnostic methodology on genomic DNA samples for sickle cell anemia.

EXAMPLE VI

5 μg of β-thalassemia, sickle cell, and normal genomic DNA was each digested with Bam H1/Taq 1 and Exo III nuclease as described in Examples 4 and 5. Linear amplification was performed as described in Example 1. Flanking oligonucleotides used were 100 fmoles of $^{32}$P-5' labeled ONS2 used directly from T4 kinase labeling reaction, without further purification, with DE-52 chromatography, and 100 fmoles of ON1. The flanking oligonucleotides were separately combined with the three templates in the presence of 200 mM NaCl and 0.5 U of T4 DNA ligase in total reaction volumes of 10 μl. The reaction mixture was incubated 3 hours at 30° C. and the reaction was terminated by boiling. A second round of amplification was initiated by adding another 0.5 U. of enzyme. The reaction mixture was again incubated 3 hours. Three rounds of ligation amplification were performed. The resulting products were then electrophoresed and autoradiographed as described above.

Figure 8:
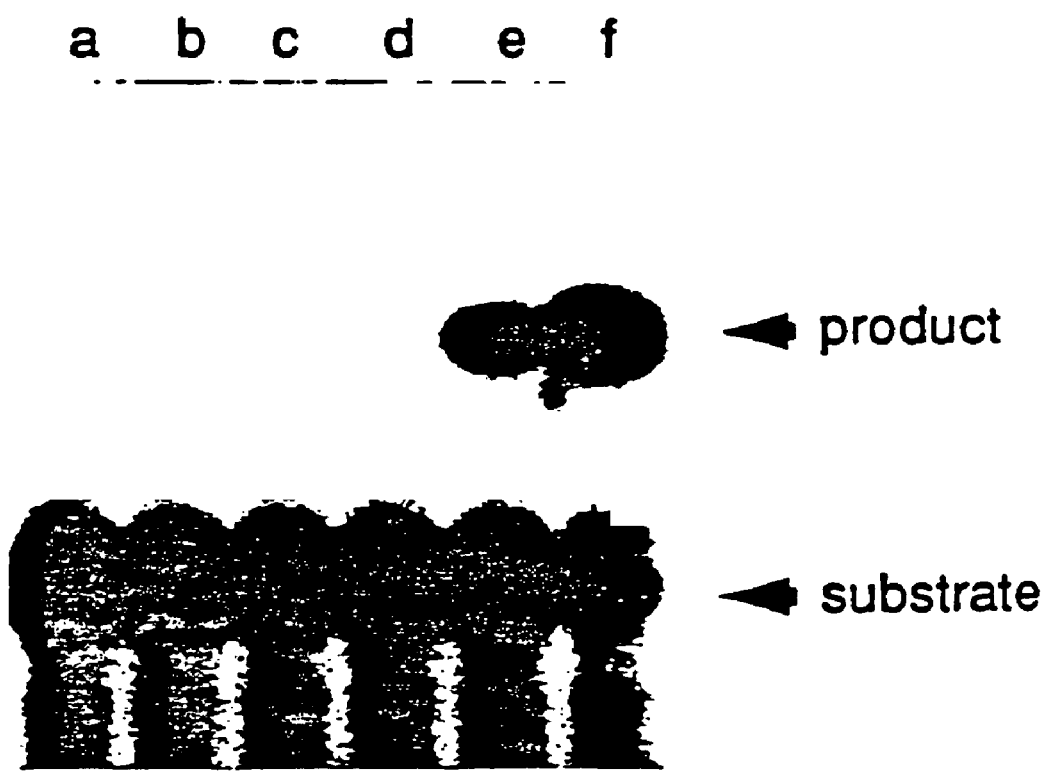
FIG. 8 is a photograph of an autoradiogram of a linear amplification resulting from the use of a pair of $\beta^S$ substrates and human genomic DNA template from β-thalassemia (lane a), sickle cell (lane b), and normal βglobin (lane c). Lanes d-f are controls.

FIG. 8 shows the resulting autoradiogram. Lane a contains reaction product using β-thalassemia template, lane b contains reaction product using sickle cell template, and lane c contains reaction product using normal beta globin template. Positive controls were performed with 0.01, 1, and 10 fmoles of Hβ19S template (lanes d-f respectively). Lane b shows the 1 expected product, whereas lanes a and c show an expected lack of product.

The methods of the present invention can also be used as a means to detect amplification product from other nucleic acid amplification methods such as the polymerase chain reaction.

EXAMPLE VII

Amplification reactions were performed with Polymerase Chain Reaction Kit (Gene Amp Kit, Perkin-Elmer Cetus) including 2.5 U of *Thermus aquaticus* DNA polymerase and 2.5 mM of oligonucleotide primers BGP1 and BGP2, 19 base long synthetic oligodeoxyribonucleotides which anneal to the beta globin gene at positions 256 nucleotides apart. The enriched 294 base pair fragment contains the β globin sequence of interest. 2 μg of the following genomic DNA were used as templates after being treated as described above: β thalassemia, homozygous sickle cell (β$^s$/β$^s$), normal β globin (β$^a$/β$^a$), and heterozygous sickle cell trait (β$^a$/β$^a$). 30 rounds of amplification gave approximately a 5×10$^5$-fold amplification of the target sequence. 10 μl aliquots of the PCR enriched genomic DNA sequences were electrophoresed in 1.5% agarose gel at 60 V for 5 hours.

The electrophoretically separated products were then transferred to Genetran nylon membranes with 20×SSC (1×SSC=150 mM NaCl and 15 mM Na citrate) according to the method of Southern, E. M. (1975).

The Genetran membranes were directly hybridized to $^{32}$P-5' labeled oligonucleotide probes Hβ19S or Hβ19A, in 5×SSPE (1×SSPE=10 mM sodium phosphate pH 7.0, 0.18 M NaCl, and 1 mM EDTA), 1% NaDodSO$_4$, 10 μg/ml of Homomix RNA, and $10^6$ cpm/ml of labeled oligonucleotide with 10 fold excess unlabelled competitor at 47° C. for 2 hours. The membrane was first washed in room temperature with 6×SSC three times for 30 minutes. Subsequent wash in TMAC1 solution for 1 hour at 59° C. removed all mismatch hybridization. (TMAC1=50 mM Tris, pH 8.0, 3 M tetramethylammonium chloride, 2 mM EDTA, 0.25% SDS).

Exponential ligation amplification was then performed on 20 μl samples of the PCR enriched sequences for 4 rounds with either 200 nM of β$^s$ substrates (ON1/ONS2 and ONS3/ON4) or 200 nM of β$^a$ substrates (ON1/ONA2 and ONA3/ON4) in a 100 μl of total reaction volume using T4 DNA ligase. 50 μl from each samples was analyzed by 20% polyacrylamide gel electrophoresis.

Figure 9:
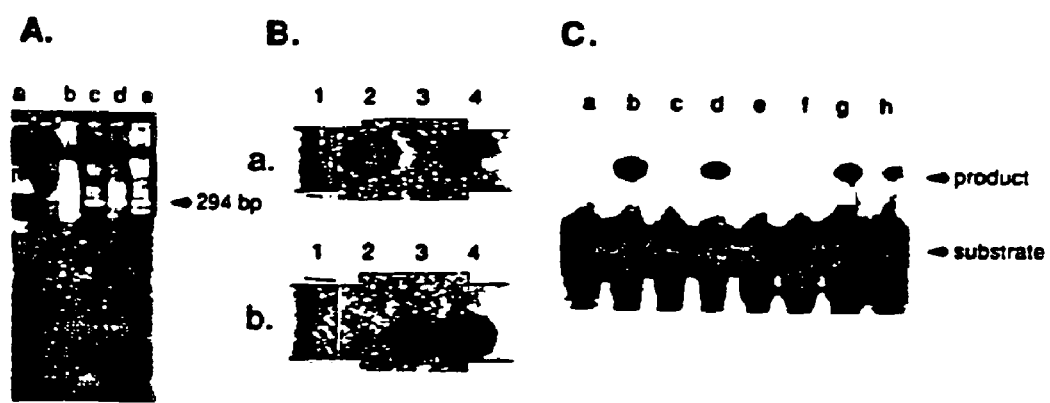
FIG. 9A is a photograph of an ethidium bromide stained agarose gel containing PCR amplified 294 base pair fragments of alleles at the human beta globin gene.
FIGS. 9B(a) and 9B(b) are photographs of autoradiograms of PCR products from the FIG. 9A gel transferred to nylon membranes and hybridized with radiolabeled Hβ19S (panel a) and radiolabeled Hβ19A (panel b) probes.
FIG. 9C is a photograph of an autoradiogram of ligation amplification products using PCR enriched sequences as templates.

Ethidium bromide staining of the 1.5% agarose gel shows a single 294 base pair band (FIG. 9A, lanes c-e). Lanes of FIG. 9A are: (a)-control; (b)-β thalassemia; (c)-homozygous sickle cell trait; (d)-normal β globin; and (e)-heterozygous sickle cell trait. PCR amplification of thalassemia DNA (Panel A lane b) amplifies some nonspecific DNA's but shows no 294 base pair band.

Oligonucleotide hybridization analysis of the PCR enriched samples (samples from lanes b-e, FIG. 9A, correspond to lanes 1-4, FIG. 9B) immobilized on Genetran nylon membrane filter confirms that the enriched DNA's indeed contain beta globin sequence of interest (FIG. 9B). Competition hybridization of the filter as described in Nozari, G., et al., Gene 43:23 (1986) with either radioactively labelled Hβ19S and unlabelled Hβ19A (FIG. 9B, panel a) or labelled Hβ19A and unlabelled Hβ19S (FIG. 9B, panel b) correctly identifies sickle cell disease (β$^s$/B$^{sβ}$, FIG. 9B, lane 2, panel a), normal (β$^a$/β$^a$, FIG. 9B, lane 3, panel 2), and sickle cell trait (β$^a$/β$^s$, FIG. 9B, lane 4, panels a and b) DNA's.

The PCR enriched 256 base pair fragments ideally serve as template in the ligation analysis since they are relatively abundant which overcomes the ligase kinetic constraints (i.e., high Km for template). Ligation amplification performed on these 294 base pair templates (FIG. 9C templates: a,e-βthalassemia; b,f-Homozygous sickle cell disease; c,g-normal β globin; d,h-heterozygous sickle cell trait) with β$^s$ (FIG. 9C, lanes a-d) flanking oligonucleotide substrates showed positive ligation for sickle cell disease and sickle cell trait samples (FIG. 9C, lanes b and d). Ligation amplification with β$^a$ (FIG. 9C, lanes e-h) flanking oligonucleotide substrates is likewise positive for normal and sickle cell trait samples (FIG. 9C, lanes g and h).

This example demonstrates that ligation amplification can be used as a detection methodology coupled to other sequence amplification techniques.

A sensitive and specific DNA sequence detection method based on the ligation of flanking oligonucleotide pairs on DNA templates and the amplification of ligated products by sequential rounds of ligation is presented. This methodology, termed the ligation amplification reaction of LAR, can be applied to detect single base-pair differences between DNA samples. In the first step of LAR, the pairs of oligonucleotide substrates are annealed to the template sequence such that one of the nucleotides at the junction is positioned at the target base of interest. When complementary base-pairing exists at the ligation junction, bacteriophage T4 DNA ligase joins the pair, forming a longer product which is bound to the template. A mismatch at the pair junction, however, prevents ligation between the two oligonucleotides. This salient feature determines the specificity of the detection reaction. Once ligated products form, subsequent amplification steps increase the products at exponential rates. Existing products are used as templates for ligation of still more substrates. If the initial ligation step does not take place as a result of a base-pair mismatch, subsequent amplification steps will not give rise to detectable ligation product. In this manner, the identification of a single base-pair differences between two DNA can be made using small amounts of genomic templates.

It is quite clear from the amplification scheme that the initial rounds are especially important in two ways. First, in initial rounds the original DNA sample is the primary template for ligation; therefore, the intrinsic specificity of the system depends on the ligase specificity in these rounds. In the later rounds, the predominant templates are the ligation products which do not contribute to single base-pair discrimination. Second, any undesirable template-independent ligation would contribute significantly to the final signal because these products could serve equally well as templates for amplification.

Both hexamers and octamers were tested as the 3' substrate for LAR. While both are equally effective as oligonucleotide substrates in the first-strand template-dependent ligation, amplification of the product occurs only with the octamer 3' substrate at 30° C. (FIG. 4). Slow second-strand ligation does occur with the hexamer substrate at 15° C., thus indicating that the 20-nucleotide-long ligation product is an inefficient template for further ligation of substrate pairs. The most likely explanation for this phenomenon is the instability of the duplex formed by the annealing of the tetradecamer substrate to the 20-nucleotide product. This duplex is stabilized only by the base-pairing of 6 complementary nucleotides and possesses one long unpaired single nucleotide strand on each side of the annealing region. At 30° C., the thermal motion of the unpaired regions is likely to destabilize the annealed region. When the reaction temperature is reduced to 15° C., this complex is more stable, hence allowing the annealing of the 3' hexamer substrate and the subsequent joining of the two oligonucleotides on the 20-nucleotide template.

The amplification aspect of this invention can be used as an amplification scheme to amplify multiple polymorphic loci simultaneously, with each locus-specific amplification product having a unique length (Skolnick and Wallace, 1988). In such a system, LAR would produce allele-specific products, thus allowing the simultaneous analysis of the genotype of the target DNA at multiple loci. Subject matter disclosed in this application is described in Wu and Wallace, (1989).

BIBLIOGRAPHY

1. Antonarakis et al., *Human Genet.* 69:1-14 (1985)
2. Cooper and Schmidtke, *Human Genet.* 73:1-11 (1986(a))
3. Cooper and Schmidtke, *Human Genet.* 77:66-75 (1986(b))
4. Wallace, et al., *Nucleic Acids Res.* 6:3543-3557 (1979)
5. Wallace, et al., *Nucleic Acids Res.* 9:879-894 (1981(a))
6. Wallace, et al., *Nucleic Acids Res.* 9:3647-3656 (1981(b))
7. Conner et al., *Proc. Natl. Acad. Sci. USA* 80:278-282 (1983)
8. Nozari, et al., *Gene* 43:23-28 (1986)
9. Wu, et al. *Gene* 76:245-254 (1989(a))
10. Wu, et al. *Genomics* 4:560-569 (1989(b))
11. Saiki, R. K., et al., *Nature (London)* 324:163-166 (1986)
12. Saiki, R. K., et al., *Science* 239:487-491 (1988(a))

13. Saiki, R. K., et al., *N. Engl. J. Med.* 319:537-541 (1988(b))
14. Impraim, et al., *Biochem. Biophys. Res. Commun.* 142:710-716 (1987)
15. Chehab, et al., *Nature (London)* 329:293-294 (1987)
16. Farr, et al., *Proc. Natl. Acad. Sci. USA* 85:1629-1633 (1988)
17. Landegren, et al. *Science* 241:1077-1080 (1988)
18. Alves and Carr, *Nucleic Acids Res.* 16:8723 (1988)
19. Wallace, R. B., et al. *Science* 209:1396 (1980)
20. Zimmerman and Phiffer *Proc. Natl. Acad. Sci. USA* 80:5852-5856 (1983)
21. Phiffer and Zimmerman *Nucleic Acids Res.* 11:7853-7871 (1983)
22. Hayashi, et al., *Nucleic Acids Res.* 14:7617-7631 (1986)
23. Takahashi, et. al. *J. Biochem.* 100:123 (1986)
24. Ferreti, et al. *Nuc. Acids Res.* 9:3695 (1981)
25. Southern, E. M., *J. Mol. Biol.* 98:503-517 (1975)
26. Skolnick, M. H. and Wallace, R. B. *Genomics* 2:273-279 (1988)
27. Wu, D. Y. and Wallace, R. B. *Genomics* 4:560-569 (1989)

The invention claimed is:

1. A method for amplifying a nucleic acid comprising a target sequence comprising the steps of:
 (i) generating a single-stranded template comprising the target sequence;
 (ii) hybridizing a pair of oligonucleotides to the template such that the oligonucleotides are juxtaposed for ligation on the template and each oligonucleotide is positioned to flank the target sequence;
 (iii) ligating the juxtaposed oligonucleotides to produce a double-stranded ligation product;
 (iv) denaturing the double stranded ligation product to produce an initial template strand and an oligonucleotide ligation product strand;
 (v) repeating steps (ii)-(iv) such that both the initial template strand and the oligonucleotide ligation stand act as templates for a further ligation reaction.

2. A method according to claim 1 wherein the single stranded template is generated by disassociating the complementary strands of a double-stranded nucleic acid.

3. A method according to claim 2 wherein both complementary strands are used as templates.

4. A method according to any one of claims 1 to 3 wherein the nucleic acid is DNA.

5. A method according to any one of claims 1 to 3 wherein the nucleic acid is RNA.

6. A method according to claim 1 further comprising producing an amplification product by repetition of step (v) and subsequently determining the presence or absence of a nucleic acid sequence complementary to or identical to the target sequence in the amplification product.

7. A method for amplifying at least one specific nucleic acid sequence in a sample containing a nucleic acid or a mixture of nucleic acids comprised of single or complementary nucleic acid strands, wherein said sample is suspected of containing said at least one specific sequence comprising:
 (a) treating the strands with at least one of two pairs of oligonucleotides which sets are complementary to at least one said specific nucleic acid sequence and flank at least one target base of a single stranded template or at least one target base pair defining a blunt end contained in said nucleic acid sequence or sequences wherein one end nucleotide of one of the oligonucleotides of at least one of said pairs is complementary to said target base or one of the bases of said target base pairs under conditions such that said end nucleotide will mutually ligate with an end of the other oligonucleotide of said pair to form a ligation product which is complementary to said specific nucleic acid sequence if said target base or target base pair is present in said sample;
 (b) treating said sample under conditions to separate ligation products from their templates if said target base or target base pairs to be detected are present in said sample; and
 (c) determining whether ligation has occurred.

8. The method of claim 7 wherein steps (a) and (b) are repeated at least once.

9. The method of claim 7 wherein a nucleic acid sequence is treated with said two pairs of oligonucleotides, and said ligation product of one of said pairs of oligonucleotides, when separated from its complement, can serve as a template for the other pair of oligonucleotides and result in an exponential formation of ligation product.

10. The method of claim 7 wherein a nucleic acid sequence is treated with only one pair of said two pairs of oligo-nucleotides and said ligation product of said one pair is separated from its complement and another of said pairs is ligated and hybridized to the same template resulting in a linear formation of ligation product.

11. The method of claim 7 wherein said ligation products are separated from their templates by denaturing.

12. The method of claim 7 wherein said nucleic acid is double stranded and its strands are separated by denaturing before or during step (a).

13. The method of claim 7 wherein a deletion or mutation of said target base or said target base pair causes a genetic disease.

14. The method of claim 13 wherein said genetic disease is sickle cell anemia.

15. The method of claim 14 wherein said pairs of oligonucleotides comprise ON1/ON2 and ON3/ON4.

16. The method of claim 14 wherein said pairs of oligonucleotides comprise ON1/ONS2 and ONS3/ON4.

17. The method of claim 7 wherein step (a) is accomplished using an enzyme selected from the group consisting of T4 DNA ligase and E. coli DNA ligase.

18. The method of claim 7 wherein said specific nucleic acid sequence is DNA.

19. The method of claim 7 wherein said specific nucleic acid sequence is RNA.

20. The method of claim 19 wherein said specific nucleic acid sequence is RNA copied into DNA by treatment with reverse transcriptase prior to step (a).

21. The method of claim 7 wherein at least one oligonucleotide of said pairs of oligonucleotides is radiolabeled.

22. The method of claim 7 wherein the reaction mixture of step (a) further comprises at least 200 mM NaCl.

* * * * *

UNITED STATES PATENT AND TRADEMARK OFFICE
CERTIFICATE OF CORRECTION

| | | |
|---|---|---|
| PATENT NO. | : 8,148,065 B1 | Page 1 of 1 |
| APPLICATION NO. | : 07/996771 | |
| DATED | : April 3, 2012 | |
| INVENTOR(S) | : R. Bruce Wallace et al. | |

It is certified that error appears in the above-identified patent and that said Letters Patent is hereby corrected as shown below:

*In the Specification*

Col. 4, line 10: "β" should be -- α- --

Col. 4, line 11: "β$_1$" should be -- α$_1$ --

Col. 4, line 22: "380B" should be -- 380 B --

Col. 4, line 28: "8to" should be -- 8 to --

Col. 4, line 31: "T4DNA" should be -- T4 DNA --

Col. 5, line 7: "(ONA1," should be -- (ON1, --

Col. 5, line 54: "BS)" should be -- (β$^S$) --

Col. 5, line 63: "product," should be -- product --

Col. 6, line 8: "$(1+\underline{x})^{(n-1)}$" should be -- $(1+\underline{x})^{(n-1)}$ --

Col. 8, line 38: "(n)(1+x)" should be -- $(n)(1+\underline{x})$ --

Col. 11, line 47: "106" should be -- $10^6$ --

Col. 12, line 45: "1 expected" should be -- expected --

Col. 12, line 63: "(β$^α$/β$^α$)" should be -- (β$^α$/β$^S$) --

Col. 13, line 39: "β$^S$/B$^{Sβ}$," should be -- β$^S$/β$^S$ --

Col. 13, line 46: "a,e-βthalassemia;" should be -- a,e -βthalassemia; --

Col. 13, line 47: "b,f-Homozygous" should be -- b,f -Homozygous --

Signed and Sealed this
Eighth Day of January, 2013

David J. Kappos
*Director of the United States Patent and Trademark Office*

```
                           SEQUENCE LISTING (1) GENERAL INFORMATION:

(iii) NUMBER OF SEQUENCES:   15

(2) INFORMATION FOR SEQ ID NO: 1:

(i) SEQUENCE CHARACTERISTICS:
          (A) LENGTH:  14
          (B) TYPE:  nucleic acid
          (C) STRANDEDNESS:   Single Stranded
          (D) TOPOLOGY:  Linear (ii) MOLECULE TYPE:   Not Applicable (iii) HYPOTHETICAL:   Not Applicable (iv) ANTI-SENSE:   Not Applicable (v) FRAGMENT TYPE:   Not Applicable (vi) ORIGINAL SOURCE:   Synthetically Prepared (vii) IMMEDIATE SOURCE:   Synthetically Prepared (viii) POSITION IN GENOME:   None (ix) FEATURE:   None (x) PUBLICATION INFORMATION:   None (xi) SEQUENCE DESCRIPTION:   SEQ ID NO: 1:

CGGCAGACTT CTCC                                                            14

(2) INFORMATION FOR SEQ ID NO: 2:

(i) SEQUENCE CHARACTERISTICS:
          (A) LENGTH:  8
          (B) TYPE:  nucleic acid
          (C) STRANDEDNESS:   Single Stranded
          (D) TOPOLOGY:  Linear (ii) MOLECULE TYPE:   Not Applicable (iii) HYPOTHETICAL:   Not Applicable (iv) ANTI-SENSE:   Not Applicable (v) FRAGMENT TYPE:   Not Applicable (vi) ORIGINAL SOURCE:   Synthetically Prepared (vii) IMMEDIATE SOURCE:   Synthetically Prepared (viii) POSITION IN GENOME:   None (ix) FEATURE:   None (x) PUBLICATION INFORMATION:   None (xi) SEQUENCE DESCRIPTION:  SEQ ID NO: 2:
```

```
TCAGGAGT                                                                    8

(2) INFORMATION FOR SEQ ID NO:3:

(i) SEQUENCE CHARACTERISTICS:
            (A) LENGTH:  6
            (B) TYPE:  nucleic acid
            (C) STRANDEDNESS:  Single Stranded
            (D) TOPOLOGY:  Linear (ii) MOLECULE TYPE:  Not Applicable (iii) HYPOTHETICAL:  Not Applicable (iv) ANTI-SENSE:  Not Applicable (v) FRAGMENT TYPE:  Not Applicable (vi) ORIGINAL SOURCE:  Synthetically Prepared (vii) IMMEDIATE SOURCE:  Synthetically Prepared (viii) POSITION IN GENOME:  None (ix) FEATURE:  None (x) PUBLICATION INFORMATION:  None (xi) SEQUENCE DESCRIPTION: SEQ ID NO: 3:

TCAGGA                                                                      6

(2) INFORMATION FOR SEQ ID NO:4:

(i) SEQUENCE CHARACTERISTICS:
            (A) LENGTH:  8
            (B) TYPE:  nucleic acid
            (C) STRANDEDNESS:  Single Stranded
            (D) TOPOLOGY:  Linear (ii) MOLECULE TYPE:  Not Applicable (iii) HYPOTHETICAL:  Not Applicable (iv) ANTI-SENSE:  Not Applicable (v) FRAGMENT TYPE:  Not Applicable (vi) ORIGINAL SOURCE:  Synthetically Prepared (vii) IMMEDIATE SOURCE:  Synthetically Prepared (viii) POSITION IN GENOME:  None (ix) FEATURE:  None (x) PUBLICATION INFORMATION:  None (xi) SEQUENCE DESCRIPTION: SEQ ID NO: 4:

ACAGGAGT                                                                    8

(2) INFORMATION FOR SEQ ID NO:5:

(i) SEQUENCE CHARACTERISTICS:
            (A) LENGTH:  6
            (B) TYPE:  nucleic acid
            (C) STRANDEDNESS:  Single Stranded
            (D) TOPOLOGY:  Linear (ii) MOLECULE TYPE:  Not Applicable (iii) HYPOTHETICAL:  Not Applicable (iv) ANTI-SENSE:  Not Applicable
```

```
        (v) FRAGMENT TYPE:  Not Applicable (vi) ORIGINAL SOURCE:  Synthetically Prepared (vii) IMMEDIATE SOURCE:  Synthetically Prepared (viii) POSITION IN GENOME:  None (ix) FEATURE:  None (x) PUBLICATION INFORMATION:  None (xi) SEQUENCE DESCRIPTION: SEQ ID NO: 5:

ACAGGA                                                                        6

(2) INFORMATION FOR SEQ ID NO:6:

(i) SEQUENCE CHARACTERISTICS:
            (A) LENGTH:  14
            (B) TYPE:  nucleic acid
            (C) STRANDEDNESS:  Single Stranded
            (D) TOPOLOGY:  Linear (ii) MOLECULE TYPE:  Not Applicable (iii) HYPOTHETICAL:  Not Applicable (iv) ANTI-SENSE:  Not Applicable (v) FRAGMENT TYPE:  Not Applicable (vi) ORIGINAL SOURCE:  Synthetically Prepared (vii) IMMEDIATE SOURCE:  Synthetically Prepared (viii) POSITION IN GENOME:  None (ix) FEATURE:  None (x) PUBLICATION INFORMATION:  None (xi) SEQUENCE DESCRIPTION: SEQ ID NO: 6:

CACCTGACTC CTGA                                                              14

(2) INFORMATION FOR SEQ ID NO:7:

(i) SEQUENCE CHARACTERISTICS:
            (A) LENGTH:  14
            (B) TYPE:  nucleic acid
            (C) STRANDEDNESS:  Single Stranded
            (D) TOPOLOGY:  Linear (ii) MOLECULE TYPE:  Not Applicable (iii) HYPOTHETICAL:  Not Applicable (iv) ANTI-SENSE:  Not Applicable (v) FRAGMENT TYPE:  Not Applicable (vi) ORIGINAL SOURCE:  Synthetically Prepared (vii) IMMEDIATE SOURCE:  Synthetically Prepared (viii) POSITION IN GENOME:  None (ix) FEATURE:  None (x) PUBLICATION INFORMATION:  None (xi) SEQUENCE DESCRIPTION: SEQ ID NO: 7:

CACCTGACTC CTGT                                                              14

(2) INFORMATION FOR SEQ ID NO:8:
```

```
        (i) SEQUENCE CHARACTERISTICS:
            (A) LENGTH:  8
            (B) TYPE:  nucleic acid
            (C) STRANDEDNESS:  Single Stranded
            (D) TOPOLOGY:  Linear (ii) MOLECULE TYPE:  Not Applicable (iii) HYPOTHETICAL:  Not Applicable (iv) ANTI-SENSE:  Not Applicable (v) FRAGMENT TYPE:  Not Applicable (vi) ORIGINAL SOURCE:  Synthetically Prepared (vii) IMMEDIATE SOURCE:  Synthetically Prepared (viii) POSITION IN GENOME:  None (ix) FEATURE:  None (x) PUBLICATION INFORMATION:  None (xi) SEQUENCE DESCRIPTION: SEQ ID NO: 8:

GGAGAAGT                                                                8

(2) INFORMATION FOR SEQ ID NO:9:

(i) SEQUENCE CHARACTERISTICS:
            (A) LENGTH:  6
            (B) TYPE:  nucleic acid
            (C) STRANDEDNESS:  Single Stranded
            (D) TOPOLOGY:  Linear (ii) MOLECULE TYPE:  Not Applicable (iii) HYPOTHETICAL:  Not Applicable (iv) ANTI-SENSE:  Not Applicable (v) FRAGMENT TYPE:  Not Applicable (vi) ORIGINAL SOURCE:  Synthetically Prepared (vii) IMMEDIATE SOURCE:  Synthetically Prepared (viii) POSITION IN GENOME:  None (ix) FEATURE:  None (x) PUBLICATION INFORMATION:  None (xi) SEQUENCE DESCRIPTION: SEQ ID NO: 9:

GGAGAA                                                                  6

(2) INFORMATION FOR SEQ ID NO:10:

(i) SEQUENCE CHARACTERISTICS:
            (A) LENGTH:  19
            (B) TYPE:  nucleic acid
            (C) STRANDEDNESS:  Single Stranded
            (D) TOPOLOGY:  Linear (ii) MOLECULE TYPE:  Not Applicable (iii) HYPOTHETICAL:  Not Applicable (iv) ANTI-SENSE:  Not Applicable (v) FRAGMENT TYPE:  Not Applicable (vi) ORIGINAL SOURCE:  Synthetically Prepared (vii) IMMEDIATE SOURCE:  Synthetically Prepared
```

-continued (viii) POSITION IN GENOME: None (ix) FEATURE: None (x) PUBLICATION INFORMATION: None (xi) SEQUENCE DESCRIPTION: SEQ ID NO: 10:

CTCCTGAGGA GAAGTCTGC                                         19

(2) INFORMATION FOR SEQ ID NO:11:

(i) SEQUENCE CHARACTERISTICS:
        (A) LENGTH: 19
        (B) TYPE: nucleic acid
        (C) STRANDEDNESS: Single Stranded
        (D) TOPOLOGY: Linear (ii) MOLECULE TYPE: Not Applicable (iii) HYPOTHETICAL: Not Applicable (iv) ANTI-SENSE: Not Applicable (v) FRAGMENT TYPE: Not Applicable (vi) ORIGINAL SOURCE: Synthetically Prepared (vii) IMMEDIATE SOURCE: Synthetically Prepared (viii) POSITION IN GENOME: None (ix) FEATURE: None (x) PUBLICATION INFORMATION: None (xi) SEQUENCE DESCRIPTION: SEQ ID NO: 11:

CTCCTGTGGA GAAGTCTGC                                         19

(2) INFORMATION FOR SEQ ID NO:12:

(i) SEQUENCE CHARACTERISTICS:
        (A) LENGTH: 23
        (B) TYPE: nucleic acid
        (C) STRANDEDNESS: Single Stranded
        (D) TOPOLOGY: Linear (ii) MOLECULE TYPE: Not Applicable (iii) HYPOTHETICAL: Not Applicable (iv) ANTI-SENSE: Not Applicable (v) FRAGMENT TYPE: Not Applicable (vi) ORIGINAL SOURCE: Synthetically Prepared (vii) IMMEDIATE SOURCE: Synthetically Prepared (viii) POSITION IN GENOME: None (ix) FEATURE: None (x) PUBLICATION INFORMATION: None (xi) SEQUENCE DESCRIPTION: SEQ ID NO: 12:

CGGCAGACTT CTCCTCAGGA GTC                                    23

(2) INFORMATION FOR SEQ ID NO:13:

(i) SEQUENCE CHARACTERISTICS:
        (A) LENGTH: 23
        (B) TYPE: nucleic acid
        (C) STRANDEDNESS: Single Stranded

```
        (D) TOPOLOGY:  Linear (ii) MOLECULE TYPE:  Not Applicable (iii) HYPOTHETICAL:  Not Applicable (iv) ANTI-SENSE:  Not Applicable (v) FRAGMENT TYPE:  Not Applicable (vi) ORIGINAL SOURCE:  Synthetically Prepared (vii) IMMEDIATE SOURCE:  Synthetically Prepared (viii) POSITION IN GENOME:  None (ix) FEATURE:  None (x) PUBLICATION INFORMATION:  None (xi) SEQUENCE DESCRIPTION: SEQ ID NO: 13:

CGGCAGACTT CTCCACAGGA GTC                                                       23

(2) INFORMATION FOR SEQ ID NO:14:

(i) SEQUENCE CHARACTERISTICS:
         (A) LENGTH:  14
         (B) TYPE:  nucleic acid
         (C) STRANDEDNESS:  Single Stranded
         (D) TOPOLOGY:  Linear (ii) MOLECULE TYPE:  Not Applicable (iii) HYPOTHETICAL:  Not Applicable (iv) ANTI-SENSE:  Not Applicable (v) FRAGMENT TYPE:  Not Applicable (vi) ORIGINAL SOURCE:  Synthetically Prepared (vii) IMMEDIATE SOURCE:  Synthetically Prepared (viii) POSITION IN GENOME:  None (ix) FEATURE:  None (x) PUBLICATION INFORMATION:  None (xi) SEQUENCE DESCRIPTION: SEQ ID NO: 14:

CCTCTTCAGA CGGC                                                                 14

(2) INFORMATION FOR SEQ ID NO:15:

(i) SEQUENCE CHARACTERISTICS:
         (A) LENGTH:  8
         (B) TYPE:  nucleic acid
         (C) STRANDEDNESS:  Single Stranded
         (D) TOPOLOGY:  Linear (ii) MOLECULE TYPE:  Not Applicable (iii) HYPOTHETICAL:  Not Applicable (iv) ANTI-SENSE:  Not Applicable (v) FRAGMENT TYPE:  Not Applicable (vi) ORIGINAL SOURCE:  Synthetically Prepared (vii) IMMEDIATE SOURCE:  Synthetically Prepared (viii) POSITION IN GENOME:  None (ix) FEATURE:  None
```

```
        (x) PUBLICATION INFORMATION:  None (xi) SEQUENCE DESCRIPTION: SEQ ID NO: 15:

TGAGGACT                                                                        8
```